United States Patent [19]
Chan et al.

[11] Patent Number: 6,048,550
[45] Date of Patent: Apr. 11, 2000

[54] HYDROPHILIC MICROPARTICLES AND METHODS TO PREPARE SAME

[76] Inventors: Daniel C. F. Chan, 3691 S. Quebec St., Denver, Colo. 80237; Paul Bunn, 630 Sundown La., Evergreen, Colo. 80439; Dmitri Kirpotin, 435 43rd Ave., Apt. 102, San Francisco, Calif. 94121

[21] Appl. No.: 08/942,758

[22] Filed: Oct. 2, 1997

Related U.S. Application Data

[60] Provisional application No. 60/027,594, Oct. 3, 1997.

[51] Int. Cl.⁷ ...................................... A61K 9/14
[52] U.S. Cl. .......................... 424/497; 424/489; 424/491; 424/493
[58] Field of Search ..................................... 424/485, 489, 424/464, 486, 490, 952

[56] References Cited

U.S. PATENT DOCUMENTS

| | | | |
|---|---|---|---|
| 4,963,367 | 10/1990 | Ecanow | 424/485 |
| 5,286,493 | 2/1994 | Oshlack et al. | 424/468 |
| 5,651,991 | 7/1997 | Sugiyama et al. | 424/502 |
| 5,853,698 | 12/1998 | Straub et al. | 424/9.52 |

FOREIGN PATENT DOCUMENTS 0 169 618 B2   11/1993   European Pat. Off. .

*Primary Examiner*—Thurman K. Page
*Assistant Examiner*—Susan Tran
*Attorney, Agent, or Firm*—Kristine H. Johnson; Macheledt Bales & Johnson LLP

[57] ABSTRACT

The present invention comprises a material and a method of its preparation. The material may be described as hydrophilic microparticles, comprising a cluster of organic substance with a layer of polyelectrolyte on its surface. The present invention establishes an improved method for preparing aqueous colloidal dispersions of water-insoluble organic substances using polyionic hydrophilic polymers by which the stability of the suspension is maintained after removal of the stabilizing and/or solubilizing medium of the drug. This improved method can be utilized to formulate a variety of water-insoluble organic substances.

16 Claims, No Drawings

HYDROPHILIC MICROPARTICLES AND METHODS TO PREPARE SAME

This application claims benefit of U.S. Provisional Application Ser. No. 60/027,594, filed on Oct. 3, 1997.

BACKGROUND OF THE INVENTION

The present invention describes submicron dispersions in water of ordinarily poorly-water-soluble organic substances. For instance, in practice of drug therapy there is a recognized need for ways to deliver water-insoluble pharmaceuticals in a stable liquid form suitable for intravenous, inhalation or other non-topical administrations. This need has been previously addressed in a number of ways including incorporation of the water-insoluble drug into micelles, delivery of suspensions of microspheres containing the drug, emulsification of the drug with oils and the use of concentrated solutions of water-soluble polymers. The same problems exist with any water-insoluble organic substances, such as pigments for staining fabrics or ink preparations.

By way of example, in the preparation of pharmaceutical formulations, the addition of surface-active agents or surfactants to an aqueous solution is used to form water soluble aggregates called micelles. These micelles contain two regions of interest a "hydrophobic core" and a hydrophilic outer shell. Compounds that are poorly soluble in water, but soluble in organic solvents can be dissolved inside the hydrophobic core of these micelles and thereby brought homogeneously into an overall aqueous medium. An example of this type of pharmaceutical formulation is the incorporation of the antifungal antibiotic Amphotericin B into micelles with the use of bile acid. Janknegt et. al., 23 *Clin. Pharm.* 279 (1992). Formulation of Amphotericin B in the micelles of deoxycholic acid is marketed for parenteral use under the name Fungizone.

A similar approach is to dissolve the drug in a vehicle which contains a concentrated solution of an amphipathic compound. Amphipathic compounds have both a hydrophobic and a hydrophilic region as part of their structure. Micelles will also be formed with the use of these compounds. On example of this type of formulation is the preparation of Cyclosporin A, an water-insoluble immunosuppressive agent used to prolong the survival of allogeneic transplants. Cyclosporin A is dissolved in Cremophor and 32.9% (w/v) of alcohol. Cremophor is a polyoxyethylated castor oil. This solution is further diluted in 0.9% sodium chloride or 5% dextrose for intravenous administration. This formulation of Cyclosporin A is marketed under the name Sandimmune IV by Sandoz Pharmaceutical Corporation.

Another way of formulating water-insoluble pharmaceuticals is to incorporate the drug into a microsphere containing a biodegradable polymer. The drug is dissolved in an organic solvent such as methylene chloride and mixed with a biodegradable polymer which is also dissolved in the organic solvent. An aqueous medium is then added to this mixture and vigorously mixed to form an emulsion. The addition of the aqueous solution causes the biodegradable polymer to precipitate. The organic solvent is then evaporated from the mixture. When the organic solvent is evaporated, solid microspheres are left behind. The microspheres are then lyophilized and can be resuspended by the addition of another aqueous solution.

Water-insoluble pharmaceuticals can also be incorporated into oil/water microemulsions to be administered parenterally. Levy et al., 54 *Int. J. Pharm.* 103 (1989). Water-insoluble organic compounds have been suspended in organic solution through a process of infusion of an aqueous precipitating liquid into an organic solvent solution which contains the organic substance of interest. EP 0 169 618 B2 (Nov. 10, 1993). Furthermore, water-insoluble organics have been suspended in gelatin or collagen. Wunderlich et. al., WO 93 10,768 (Jun. 10, 1993). However, gelatin is inherently hydrophilic and the disclosure requires that the resulting particle be electrically neutral so as to enhance oral adsorption. The particle will therefore be hydrophobic in this neutral state. The present invention, due to a net charge in the final product, has improved solubility, biodistribution and kinetics.

All of the above mentioned known approaches to delivering water-insoluble pharmaceuticals have one common disadvantage to their use. The presence of substantial amounts of surfactant, water soluble polymer, amphipathic compounds etc., in the delivery vehicle can cause vehicle-associated toxicity. The use of Cremophor in the formulation of Cyclosporin A (Sandimmune IV) has been shown to cause anaphylactoid reactions (19 *Intell. Clin. Pharm.* 425 (1985)) and the use of surfactants like bile acids for the delivery of Amphotericin B is known to cause the lysis of red blood cells (Forster and Davis, 40 *J. Pharm. Pharmacol.* 325 (1988)) and increased nephrotoxicity (Inselman et. al., 14 *Renal Failure* 17 (1992)).

Any method that improves the delivery of water-insoluble pharmaceuticals such that the risk of vehicle-associated side effects is reduced would be of great value to the medical community. The purpose of this invention is to show that the amount of stabilizing and/or solubilizing vehicle of a water-insoluble pharmaceutical can be reduced and still be able to be properly delivered thereby lower the risk of vehicle-associated side effects caused by the current formulations.

SUMMARY OF THE INVENTION

The methods of the present invention utilize a specific class of hydrophilic polymers called polyelectrolytes to stabilize water-insoluble organic compounds from aggregation and flocculation. Any water-insoluble organic compounds are amenable to the present invention, including pigments, magnetic particles and pharmaceuticals. When used in the pharmaceutical field, the present invention differs from previously described methods to prepare pharmaceutical dispersions in that the bulk of the stabilizing polyelectrolyte which are not complexed with the pharmaceutical may be removed from the pharmaceutical dispersion without any loss in the stability of the dispersion. In contrast, such removal of the stabilizing or solubilizing vehicle from the previously described methods would disrupt the dispersion and result in the inability to properly deliver the drug. Therefore, the ability to remove the bulk of the stabilizing vehicle from the invented drug formulation helps to reduce the amount of such vehicle to be administered to the body along with the drug and thereby reduces the potential for vehicle-associated side effects.

The invention relies on specialized method to prepare compositions of matter with specific characteristics. The starting materials of the present invention, the water-insoluble organic compound and the polyelectrolyte, must possess the characteristics of net charges which are opposite to each other. For example, if the organic compound has a net negative charge, the polyelectrolyte must have a net positive charge. The methods to convert these starting materials to final product is disclosed in the examples, and relies on a novel process which avoids flocculation. Moreover, the final product bears a net charge, which is beneficial for a variety of uses. In particular, in the pharmaceutical field, a net charge on a water-soluble drug (which would, without the special processing described in the present invention, be water-insoluble) provides therapeutic benefits.

It is therefore an object to provide water-soluble compositions of matter comprising at least one cluster of water-insoluble organic compound having a net charge complexed with a polyelectrolyte having an opposite net charge.

In one broad aspect of the invention, there is provided pharmaceutical dispersions having reduced potential for vehicle-associated side effects.

It is also an object to provide a method for reducing the amount of vehicle needed to prepare an aqueous colloidal dispersion in order to deliver water-insoluble organic compounds via injection, inhalation or other non-topical routes of administration.

It is yet another object to provide a method to prepare pharmaceutical microparticles of water-insoluble drugs using hydrophilic polymers in which the water-insoluble drug forms a stable colloid in an aqueous medium.

It is yet another object to provide a method to prepare aqueous colloidal suspensions for water-insoluble chemotherapeutic agents.

It is yet another object to provide a method to prepare aqueous colloidal suspensions for water-insoluble organic pigments useful in paints, inks and organic dyes.

It is yet another object to provide a method to prepare aqueous colloidal suspensions for water-insoluble systemic antimicrobial agents.

It is yet another object to provide a method to prepare aqueous colloidal suspensions for water-insoluble pharmaceuticals in general, that are suitable for injection, inhalation or other non-topical route of administration.

Other objects and features of the present invention will be apparent from the following detailed description.

DETAILED DESCRIPTION OF THE INVENTION

The present invention comprises a material and a method of its preparation. A composition of matter is provided which is a water-soluble microparticle with a net charge, comprising a cluster of water-insoluble organic substance with one net charge complexed with polyelectrolyte with a net charge opposite that of the organic substance and microparticle. Preferably, the microparticle is 0.03–5 microns in size. These microparticles form a stable colloid in an aqueous medium. Most preferred microparticles are from 0.5–2 microns in size.

In general, any pharmaceutical which combines lipophilic properties, resulting in low water solubility, with the presence of ionizable groups in their molecular structure, are within the scope of the invention. Examples of such ionizable groups are: amino, amidino, guanidino, azo, nitrogen-containing heterocyclic, phenolic, thiol, thiophenolic, carboxylic, 1,2-unsaturated alcohol (enol), Ithiocarboxylic, dithiocarboxylic, sulfo-, sulfonic, sulfinic, thiosulfonic, phosphine, phosphate, phosphonic, phosphinic, thiophosphonic and thiophosphate groups. Compounds with lipophilic properties are, for example, those containing aromatic, condensed aromatic, alicyclic, medium- and long chain aliphatic groups, or combinations thereof.

For example, such pharmaceutical may be Dexinuguldipine, a drug known to increase the sensitivity of drug-resistant cancer cells to anticancer chemotherapy. Hoffman et. al., 49 *Biochem Phamacol.* 603 (1995). Another example of such insoluble pharmaceutical is Clofazimine, an antimycobacterial agent. Garrelts, 25 *DICP, The Annals of Pharmacotherapy* 425 (1991). Yet another example is Miconazole, an antifungal agent. *Physician's Desk Reference* (1995). All these pharmaceutical agents are water-insoluble, hydrophobic substances which posses, however, ionizable groups that vest into them the ability to undergo ionic dissociation and form ionic charges of the positive sign in an aqueous environment.

Following is a list exemplifying pharmaceuticals which are poorly soluble in water at appropriate pH (6–8) and have ionizable groups in their molecular structure from *American Hospital Formulary Service, Drug Information,* 1996 edition, and British Pharmacopoeia 1993–1996. This list does not include all investigational drugs and drugs not approved for use in the U.S. as of 1996, although those with similar properties are considered as within the scope of the present invention.

1. Antihistamines: loratadine, terfenadine, famotidine, cyproheptadine, buclizine, cinnarizine.

2. Amebicides: iodoquinol, mebendazole, thiabendazole, oxamniquine, timidazole.

3. Antifungal: amphotericin B, imidazole derivatives (butoconazole, clotrimazole, econazole, itraconazole, ketoconazole, miconazole, oxiconazole, terconazole), gentian violet, nafbifine, terbinafine, clioquinol.

4. Anti-mycobacterial: rifabutin, clofazimine.

5. Anti-malarial: pyrimethamine, sulfadoxine.

6. Antimicrobial quinolones: nalidixic acid.

7. Antimicrobial sulfonamides: sulfadiazine, sulfamethazole, sulfamethoxazole, sulfalazine, sulfaxazole, sulfadimidine, sulfafurazole, silfasomidine.

8. Anti-viral: saquinavir, ritonavir, indinavir, idoxuridine.

9. Antineoplastic: melphalan, mercaptopurine, thioguanine.

10. Adrenergic: salmeterol.

11. Anticoagulants: dicumarol, nicoumalone.

12. Antiarrhythmic: disopyramide (take out amiodarone!).

13. Dihydropyridines (Calcium channel blockers): nicardipine, nifedipine, nimodipine, felodipine, niguldipine, and their dex-enantiomers.

14. Anti-hypertensive: reserpine and its derivatives, pindolol, prazolin.

15. Antilipidemic: fluvastatin, gemfibrozil, pravastatin.

16. Non-steroid anti-inflammatory: salsalate, etodolac, ibuprophen, indomethacin, ketoprophen, mephenamic acid, piroxicam, naproxen, azapropazone.

17. Anxiolytic: benzodiazepines (clonazepam, bromazepam, alprazolam, estazolam, lorazepam, oxazepam, quazepam).

18. Antipsychotic: haloperidol, primozide, droperidol, fluphenazine, sulpiride, perphenazine, flupenthixol.

19. Diuretic: thiasides (bendroflumethazide, chlorotiazide, hydrochlorothiazide, hydroflumethiazide, polythiazide), metholazone, furosemide, pteridines (triamterene).

20. Hypoglycaemic sulfonureas: glipizide, tolazamide, gliclazide, glibenclamide.

21. Oxytocics: prostaglandines (dinoprostone).

22. Antiprutitics and alangesics: dibucaine, phenazopyridine.

23. Retinolc acid derivatives: tretinoin, isotretinoin.

24. Piperidinopyrimidine vasodilators/hair growth stimulants: minoxidil.

25. Vitamins: riboflavin, folic acid.

26. Ovulation inducers: clomiphene.

27. Antipsoriatic: dithranol.

28. Antiemetic: domperidone, cyclizine.

29. Antiestrogens: tamoxifen.

30. Platelet aggregation inhibitors: ticlodipine, dipyridamole.

31. Hypnotic: zopiclone, metaqualone.

32. Drugs for treatment of peptic ulcer: omeprazole, sulfazalazine.

33. Antidiarrheal: dipenoxylate.

34. Anti-gout and anti-thyroid: allopurinol, propylthiouracil.

35. Immunosupressant: azathioprine.

36. Steroids: hydrocortizone hydrogen succinate, stanozolol.

37. Cough supressant: noscapine.

38. Anorexogenic: dexfenfluramine.

In addition, the inventive material may include useful organic substances other than pharmaceutical, such as, for example: organic pigments used in fabric dyeing, inks, paints, as fillers for colored plastics, etc.; volume-increasing, gas producing substances, used in production of foams and in food industry, and in other applications where stable, aqueous-based organic colloids are desirable.

Polyelectrolytes suitable for the purpose of the invention are, in general, polymer molecules, that is, molecules consisting of repetitive units of similar chemical structure, with molecular weights—roughly defined—from 400 to 2,000,000, soluble in water, and containing in their structure ionizable groups, that is, chemical functional groups capable of electrolytic dissociation resulting in the formation of ionic charge. Examples of such ionizable groups are given above in the characterization of pharmaceuticals. It is essential that in any material according to the invention, net charge of the polyelectrolyte is the opposite to that of the pharmaceutical.

The following list gives examples of such polyelectrolytes.

1. Acidic and basic polysaccharides—natural and derived from natural: polygalacturonates, gialuronic acid, gum arabic, chondroitin sulfates A, B, and C, keratan sulfates, dermatan sulfates, heparin and its derivatives, pectin and its derivatives, alginic (poly-anhydromannuronic) acid, teichoic acids, chitosans; derivatives of cellulose, amylose, amylopectin, dextran, or other neutral polysaccharide obtained by introduction of carboxyalkyl, phosphate, sulphate, amino-, mon-, di-, trialkylamino, tetraalklammonium functional groups, derivatives of the said polysaccharides with nitrogen heterocycles, and derivatives obtained by grafting other ionizable functions to polysaccharide backbone.

2. Acidic and basic polypeptides and proteins, synthetic or natural: polymers and copolymers containing glutamic acid, aspartic acid, lysine, arginine, ornitine, other nonprotein amino acids with ionizable funtion in the side chain; proteins with extremely high or low isoelectric points, such as cytochrome C, histone, protamine, trypsin, and partially hydrolyzed collagens.

3. Nucleic acids, oligo- and polynucleotides, and their derivatives.

4. Polymeric carboxylic acids: polymers and copolymers containing units of acrylic acid, methacrylic acid, maleic acid, propargylic acid, styrenecarboxylic acid, or other alkenyl- or alkenylarylcarboxylic acid; polymers and copolymers containing ionizable carboxyls in side groups on a polyamide, polyether, polyester, or polycyclic backbone.

5. Polymers with phosphate groups in the polymer backbone, such as polyphosphates, or in side chains, such as polyvinylphosphate.

6. Polymers bearing sulfo groups, such as: polyvinylsulfate, polyvinylsulfonate, polystyrenesulfonate, sulfated rosin gum (naphtenate).

7. Polymeric amines and amino containing heterocycles, whether in side groups or in the polymer backbone, such as: polyvinylamines, polyallylamines, polyvinylalkylamines and polyvilyltrialkylammonium salts, polyvinylpyridines, quaternized polyvinylpyridines, poly(alkylene immines), quaterinzed poly(alkylene imines), poly(aminoalkyl) acrylates, poly (alkylaminoalkyl) acrylates, poly (aminoalkyl) vinyl alcohols, and copolymers containing the units of the above polymers.

8. Polymers containing thiocarboxylic, dithiocarboxylic, thiosulfate, and thiophosphate functions in side chains or in the main polymer backbone.

The polyelectrolytes, according to the invention, may be, for example, polymeric carboxylic acid, such as polyacrylic acid, or polysaccharides, such as chondroitin sulfate A or dextran sulfate. These compounds are polymers that are soluble in water, and in such solution they acquire multiple ionic charges of the negative sign. It is understood that the present invention is not limited to the above illustrative compounds.

The mechanism of drug dispersion and stabilization is explained by the formation of stable multiple ionic interactions between the charged groups of the polyelectrolyte and the opposite charges on the surface of the drug aggregates that are created when the colloidal suspension is formed. These interactions provide a dual purpose. First, they prevent further growth of the drug particles keeping them in a submicron size suitable, for example, for aerosol formulations. This makes the particles capable of passing through blood capillaries in the body. Secondly, the ionic interactions provide a thin, stable hydrophilic coating tightly associated with each drug colloidal particle which makes it unnecessary to retain the excess stabilizing and/or solubilizing vehicle in the resulting formulation.

The present invention establishes an improved method for preparing aqueous colloidal dispersions of water-insoluble organic substances using polyionic hydrophilic polymers by which the stability of the suspension is maintained after removal of the stabilizing and/or solubilizing medium of the drug. This improved method can be utilized to formulate a variety of water-insoluble organic substances.

For example, an aqueous colloidal dispersion is formed by first dissolving a pharmaceutical of choice in a suitable water-miscible solvent such as dimethylsulfoxide. A hydrophilic polymer which is of opposite charge to the drug is dissolved in a suitable aqueous solution (i.e., 0.9% sodium chloride buffered at pH=7.4). These two solutions are then mixed together with agitation. The colloidal phase of the mixture is separated by filtration or centrifugation. The separated colloidal microparticles are resuspended in a suitable aqueous vehicle for administration. The obtained colloid may be lyophilized for storage and further reconstituted in aqueous solution suitable for further use.

The following examples are for illustrative purposes only, and are not intended to limit the scope of the invention in any way.

EXAMPLES

1) Colloidal Dispersion of Dexniguldipine 85 mg of Dexniguldipine Hydrochloride (BYK Gulden pharmaceuticals) was dissolved in 4 mL of 50% aqueous dimethylsulfoxide (DMSO). 150 mg of Chondroitin Sulfate A was dissolved in 11.5 mL of normal saline buffered with 20 mM HEPES-Na buffer, pH=7.4 (HEPES-NS). The Dexniguldipine Hydrochloride solution was added to the of Chondroitin Sulfate A solution while stirring. The resulting mixture was stirred for 2 minutes. After which the mixture was allowed to sit for 15 minutes. The mixture was then filtered using a 0.2 micrometer cellulose acetate filter. The remaining pellet was transferred into 8 mL of HEPES-NS and dispersed in an ultrasonic bath (duration 5 seconds). Stable colloidal dispersion of the drug was produced. The z-average size of drug particles measured by quasi-elastic light scattering was 0.505 micrometer. Under these conditions, the addition of the Dexniguldipine Hydrochloride solution to the HEPES-NS without the addition of Chondroitin Sulfate A yields a gross flaky precipitate.

The pellet of Chondroitin Sulfate A-treated Dexniguldipine Hydrochloride containing 10 mg of the drug was obtained as described above and redispersed in 1 mL of deionized water. 50 mg of Dextrose was added to this solution and the mixture was lyophilized. The dry product was then reconstituted in 1 mL of water to give a stable submicron dispersion with the z-average particle size of 1.19 micrometer as measured by quasi-elastic light scattering.

Various other hydrophilic polymers were investigated for there use in producing dispersions of Dexniguldipine Hydrochloride. 0.1 mL of a solution containing 2 mg/mL Dexniguldipine Hydrochloride in 50% aqueous DMSO was added to 1 mL of HEPES-NS containing 10 mg of one of the following polymers: Chondroitin Sulfate A, Dextran Sulfate, polyacrylic acid sodium salt (MW 150,000), polyacrylic acid sodium salt (MW 2000) or Dextran (MW 70,000). A control group containing no polymer was also investigated. Each mixture was vortexed for 1 minute and allowed to sit for 24 hours at room temperature. After this time period the mixtures were votexed again for 15 minutes after which the quality and stability of the dispersions were visually evaluated. Stable dispersions were produced only in the mixtures that contained polyanions.

2) Colloidal Dispersion of Clofazimine 10 mg of Clofazimine was dissolved in 1 mL of DMSO and added to 10 mL of a solution containing 100 mg of Chondroitin Sulfate A in HEPES-NS while vortexing. The mixture was then filtered using a 0.2 micrometer cellulose acetate filter. The remaining pellet was redispersed in 5 mL of deionized water by vortexing. Stable dispersion of the drug was produced with the z-average particle size of 0.327 micrometer. To this solution, 50 mg of lactose monohydrate was added and the mixture was lyophilized. The dry product is then reconstituted in water to give a stable submicron dispersion of Clofazimine with the z-average particle size of 0.298 micrometers (measured by light scattering). The same procedure without the use of Chondroitin Sulfate A results in gross precipitation of Clofazimine.

3) Colloidal Dispersion of Miconazole 10 mg of Miconazole was dissolved in 0.5 mL of DMSO and added to 10 mL of 25 a solution containing 100 mg of Chondroitin Sulfate A in HEPES-NS while vortexing. The remaining pellet was redispersed in 5 mL of deionized water by vortexing. In the presence of Chondroitin Sulfate A a submicron dispersion was formed. While in the absence of Chondroitin Sulfate A, a coacervate-like spheroid precipitate was formed.

We claim:

1. A microparticle consisting essentially of: a molecular cluster of water-insoluble organic substance with ionizable groups capable of imparting a net charge, complexed with a layer of polyelectrolyte with ionizable groups capable of imparting a net charge opposite that of the organic substance, whereby said microparticle comprises a non-zero net charge and is stably dispersible in water.

2. A microparticle of claim 1, wherein the microparticle is 0.03–5 microns in size.

3. A microparticle of claim 2, wherein the microparticle is 0.5–2 microns in size.

4. A microparticle of claim 1, wherein the organic substance is a pharmaceutical.

5. A microparticle of claim 4, wherein the pharmaceutical is selected from the group consisting of dexiniguldipine, clofazimine and miconazole.

6. A microparticle of claim 1, wherein the organic substance is an organic pigment.

7. A microparticle of claim 1, wherein the polyelectrolyte is a polymeric acid.

8. A microparticle of claim 1, wherein the polyelectrolyte has a molecular weight in the range of 400 to 2,000,000 daltons.

9. A microparticle of claim 1, wherein the polyelectrolyte is selected from the group consisting of acidic polysaccharides, basic polysaccharides, acidic polypeptides, basic polypeptides, acidic proteins, and basic proteins.

10. A microparticle of claim 1, wherein the polyelectrolyte is selected from the group consisting of: polymeric carboxylic acid, polyacrylic acid, chondroitin sulfate, and dextran sulfate.

11. A method to make stable aqueous colloidal dispersions of ionizable, poorly-water-soluble organic substances, comprising:

a.) dissolving a poorly-water-soluble organic substance in a suitable water-miscible organic solvent;

b.) dissolving a polyelectrolyte of an opposite charge to that of the organic substance in a suitable aqueous solution;

c.) mixing solutions formed from steps a.) and b.) to form a colloidal phase and a solvent phase;

d.) separating colloidal phase of step c.) from the solvent and excess polyelectrolyte; and f.) resuspending the colloidal phase in a suitable aqueous solution.

12. A method of claim 11, which further comprises the steps of g.) lyophilizing the resuspended colloidal phase; and h.) reconstituting lyophilized colloidal phase in a suitable aqueous vehicle for medical administration.

13. A method of claim 12, wherein the organic substance is a pharmaceutical.

14. A method of claim 13, wherein the organic substance is selected from the group consisting of: dexniguldipine, clofazime, and miconazole.

15. A method of claim 4, wherein the polyelectrolyte is a polymeric acid.

16. A method of claim 15, wherein the polyelectrolyte is selected from the group consisting of: polyacrylic acid, chondroitin sulfate, and dextran sulfate.

* * * * *

UNITED STATES PATENT AND TRADEMARK OFFICE
CERTIFICATE OF CORRECTION

PATENT NO. : 6,048,550  
DATED : April 11, 2000  
INVENTOR(S) : Daniel C.F. Chan, Dmitri B. Kirpotin and Paul A. Bunn It is certified that error appears in the above-identified patent and that said Letters Patent is hereby corrected as shown below:

Title page,
Item [60], Related U.S. Application Data, change "1997" to -- 1996 --.

Column 1,
Line 5, replace "1997" with -- 1996 --.

Signed and Sealed this

Fourth Day of March, 2003

JAMES E. ROGAN
*Director of the United States Patent and Trademark Office*